United States Patent
Kavala et al.

(10) Patent No.: US 11,161,853 B2
(45) Date of Patent: Nov. 2, 2021

(54) METHOD FOR ISOLATION AND PURIFICATION OF NALTREXONE

(71) Applicant: SANECA PHARMACEUTICALS A.S., Hlohovec (SK)

(72) Inventors: Miroslav Kavala, Leopoldov (SK); Dušan Vandák, Modra (SK); Miroslav Palík, Bratislava (SK); Ján Gašpar, Bratislava-Dúbravka (SK); Richard Hercek, Hlohovec (SK)

(73) Assignee: SANECA PHARMACEUTICALS A.S., Hlohovec (SK)

( * ) Notice: Subject to any disclaimer, the term of this patent is extended or adjusted under 35 U.S.C. 154(b) by 10 days.

(21) Appl. No.: 16/340,596

(22) PCT Filed: Oct. 6, 2017

(86) PCT No.: PCT/SK2017/000008
§ 371 (c)(1),
(2) Date: Apr. 9, 2019

(87) PCT Pub. No.: WO2018/070943
PCT Pub. Date: Apr. 19, 2018

(65) Prior Publication Data
US 2020/0048271 A1    Feb. 13, 2020

(30) Foreign Application Priority Data

Oct. 11, 2016 (SK) .............................. PP 5028-2016

(51) Int. Cl.
*C07D 491/08* (2006.01)
(52) U.S. Cl.
CPC ........ *C07D 491/08* (2013.01); *C07B 2200/13* (2013.01)
(58) Field of Classification Search
CPC .................................................. C07D 491/08
USPC ......................................................... 546/47
See application file for complete search history.

(56) References Cited

U.S. PATENT DOCUMENTS

| 3,332,950 A | 7/1967 | Blumberg |
| 4,141,897 A | 2/1979 | Olofson et al. |
| 2010/0021675 A1 | 1/2010 | Hasegawa et al. |
| 2011/0257401 A1 | 10/2011 | Sato et al. |
| 2011/0272681 A1 | 11/2011 | Sugimoto et al. |

FOREIGN PATENT DOCUMENTS

| EP | 2 813 507 | 12/2014 | |
| JP | WO 2004046075 | * 6/2004 | ............ C07B 63/00 |
| JP | 2004-256434 | 9/2004 | |
| JP | 2005-289836 | 10/2005 | |
| JP | 2009-185187 | 8/2009 | |
| JP | 2010-195745 | 9/2010 | |
| JP | 2010-229042 | 10/2010 | |
| RU | 2505542 | 1/2014 | |
| WO | WO2004/108084 | 12/2004 | |
| WO | WO2006/121106 | 11/2006 | |
| WO | WO 2006/135650 | 12/2006 | |

OTHER PUBLICATIONS

Watanabe, Organic Process Research & Development 2007, 11, 251-258.*
Watanabe, K., Organic process research & development, 2007, 11, 251-258.
"Narcotic Antagonists: Naltrexone Pharmacochemistry and Sustained-Release Preparations", NIDA Research Monographs, Jan. 1, 1981, pp. 1-277, XP055426237.
International Search Report issued for PCT/SK2017/000008, dated Dec. 20, 2017.

* cited by examiner

*Primary Examiner* — Nizal S Chandrakumar
(74) *Attorney, Agent, or Firm* — Mark S. Cohen; Pearl Cohen Zedek Latzer Baratz

(57) ABSTRACT

The invention describes a method for purification of naltrexone base from reaction mixtures concentrated by evaporation and/or from mixtures containing naltrexone in the presence of other organic or inorganic substances by trituration and/or extraction and crystallization from cyclopentyl methyl ether (CPME), optionally from a mixture of cyclopentyl methyl ether and another organic solvent. Naltrexone of high purity is obtained by this method and can be used in a parenteral dosage form.

15 Claims, No Drawings

METHOD FOR ISOLATION AND PURIFICATION OF NALTREXONE

CROSS-REFERENCE TO RELATED APPLICATIONS

This application is a National Phase Application of PCT International Application PCT/SK2017/000008, filed Oct. 6, 2017, claiming priority to and the benefit of Slovakia Patent Application PP 5028-2016, filed Oct. 11, 2016, both of which are incorporated by reference herein in their entirety.

FIELD OF INVENTION

The invention is from the field of pharmaceutical manufacture. It relates to preparation and purification of naltrexone which is used as opioid analgesic antagonist.

BACKGROUND OF THE INVENTION

Naltrexone, structure (1), and its salts, such as naltrexone hydrochloride, are active pharmaceutical ingredients (API) which are used particularly for reduction of psychological dependence in patients with drug addiction.

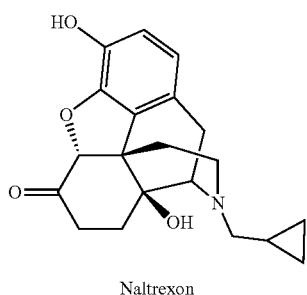

Naltrexon (1)

Naltrexone can be isolated or purified by crystallization or precipitation. Several methods for purification (described in the patents bellow) are known in the patent literature, using polar, non-polar, protic, as well as aprotic solvents.

U.S. Pat. No. 3,332,950 describes preparation of naltrexone base by precipitation from water with subsequent recrystallization from acetone. Data on purity or content of the product are not reported.

U.S. Pat. No. 4,141,897 describes naltrexone synthesis. Naltrexone is obtained from reaction mixture by extraction into chlorinated solvents (dichloromethane and chloroform) with subsequent evaporation to dryness. The distillation residue is crystallized from acetone. More detailed data on purity or content are not reported.

WO2004/108084 describes solvates of naltrexone with benzyl alcohol, dimethylformamide, methanol, dichloromethane, acetone, ethyl acetate, toluene, hexane and naltrexone monohydrate prepared by fast or slow cooling of naltrexone solutions in an appropriate solvent which are characterized with powder X-ray, DSC data, and IR spectra.

In WO2004/108084, monohydrate of naltrexone base was prepared by fast cooling of water solution. The monohydrate is characterized with powder X-ray, DSC data, and IR spectrometry. Purity or content are not specified in more detail in the patent.

US2010021675 describes solvent-free form of naltrexone which is characterized with powder X-ray record. By the term "solvent-free" the authors mean the form which is neither a hydrate nor a solvate. The subject matter of the invention is a physical form of naltrexone which is a stable product with a high HPLC purity, which, however, is not specified in more detail. A method for the preparation of such form from any substrate containing naltrexone is also described (preferably from a mixture which contains at least 80% of naltrexone) which is dissolved at higher temperature in a solvent containing at least one ester group or in a mixture of such solvents. The authors report in their description ester compounds, such as methyl acetate, ethyl acetate, methyl butyrate, methyl benzoate, etc.

Authors of patent RU2505542 have found that naltrexone base in the form of hemihydrate can be prepared with a high yield by simple stirring of anhydrous naltrexone base suspension during specified period without need of dissolution, alternatively by heating and subsequent filtering of naltrexone hemihydrate.

In most cases, the yields and purity of the naltrexone obtained are not reported.

Based on the patent search, patents using cyclopentyl methyl ether for extraction or crystallization of various compounds with non-opioid basic structure were found (WO2006/121106—Method for producing indole derivative having piperidine ring, JP2009-185187—Manufacturing method for alkylphenol-formaldehyde co-condensed resin, JP2010-229042—Method for producing Laurolactam, US2011/0257401—Process for producing optically active carboxylic acid, US2011/0272681—light emitting element material and light-emitting element, JP2010-195745—Method for producing γ-ketoacetal compound and pyrrole derivative, JP2005-289836—Method for purifying Iopamidol a JP2004-256434—Method for purifying 2,5-dihydroxybenzoic acid).

SUMMARY OF THE INVENTION

No use of ethers for extraction and crystallization of naltrexone base is described in the literature. Investigating the possibilities of using ethers, we have found that naltrexone base either has poor solubility, is poorly purified by crystallization from these solvents, or its yields are low. Surprisingly, it was found that the use of cyclopentyl methyl ether of structure 2 (CPME) for crystallization of naltrexone overcomes the prior art and leads to the yield of white to light beige product with high purity and content above 98% (HPLC). This property can also be employed in recrystallization of naltrexone base with purity below 80% by weight, when usually one crystallization is sufficient; if higher purity is necessary, repeated crystallization can be used. An advantage is that naltrexone base has good solubility in cyclopentyl methyl ether already at slightly elevated temperatures (diluted solutions) or at elevated temperatures (concentrated solutions) which can be used for example in isolation of the product from the reaction mixture. In mixtures where the naltrexone base is the major product (besides organic solvents), cyclopentyl methyl ether can be used for extraction, wherein extract thus obtained can be directly used for crystallization without additional adjustments, alternatively following effective removal of water with azeotropic distillation of the mixture of cyclopentyl methyl ether-water.

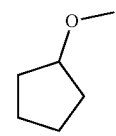

Cyklopentylmetyléter
(CPME)

Cyclopentyl methyl ether itself has relatively many advantages which put it in the position of a new industrial solvent acceptable for the environment (Watanabe, K., Organic process research & development, 2007, 11, 251-258). Cyclopentyl methyl ether can be easily dehydrated azeotropically, formation of (hydro)peroxides is suppressed due to the structure, it is relatively stable under acidic as well as basic conditions, it has low evaporation energy and narrow range of explosiveness. All these properties are appropriate for industrial utilization.

Crystallization can be normally performed in a simple device, also in large volumes and with high yields (more than 80%). A product with a low water content (less than 1%) is thus obtained, and if the solution is dehydrated azeotropically before crystallization, water content in naltrexone base may decrease below 0.1%.

Naltrexone base thus obtained is used in a dosage form, preferably in a parenteral dosage form, such as a patch. Naltrexone base thus obtained is used for the preparation of appropriate salts which are used in dosage forms.

DETAILED DESCRIPTION

This invention is defined in the patent claims.

Term Definition

Trituration—means stirring a compound in a solvent in the form of suspension, wherein soluble impurities remain in the solution and crystalline substance is enriched by its main poorly soluble component.

The use of cyclopentyl methyl ether for the crystallization of naltrexone base containing approx. 75% by weight provides good results (a product containing 95 to 96% by weight is obtained). In case that such quality is not sufficient, it is possible to repeat the crystallization with cyclopentyl methyl ether, wherein content of thus recrystallized product increases to 98% by weight or more. Naltrexone thus obtained has HPLC purity and content depending on the purity and the content of starting substrate, but preferably more than 93%. In the best case, optionally by repeated crystallization, a product with HPLC purity of naltrexone 99.8% and more and with the content above 99.0% by weight is obtained. For crystallization, dry or wet cyclopentyl methyl ether can be used. Crystallization yields are achieved in the range of 40 to 95%.

Procedures for the preparation, isolation and purification of naltrexone with the solvent used for isolation and purification being the same solvent from the group of ethers are not described in the literature. Surprisingly, we have found that relatively good solubility of naltrexone base in cyclopentyl methyl ether compared to the other ethers (e.g., diethyl ether, di-n-butyl ether or tert-butyl methyl ether) can be advantageously used also in isolation of naltrexone from the reaction mixture, wherein additional surprising fact is a significantly better purification ability and better yields (see Table 1). In the reactions where the major product or one of the products is naltrexone base, the reaction mixture can be extracted with cyclopentyl methyl ether for the purpose of its isolation. An advantage of the extraction of naltrexone base with cyclopentyl methyl ether is that it does not extract very polar substances (impurities), and the extraction itself presents a step of purification. After separation, the organic phase can be left to crystallize directly, optionally a part of the solvent can be evaporated to increase the crystallization yield and dehydration.

In both the above mentioned cases, naltrexone solution can be left to crystallize spontaneously, but crystallization can also be induced by inoculation.

As in the case of extraction, pure cyclopentyl methyl ether which may be dry as well as wet (water content 0.01 to 2%) also can be used for crystallization. The relatively small content of water which cyclopentyl methyl ether is able to dissolve has no significant impact on the purification selectivity or the yield of extraction or crystallization.

In the use of cyclopentyl methyl ether in extraction of naltrexone base, the base already may be as a suspension in aqueous environment and subsequently it is dissolved in cyclopentyl methyl ether or cyclopentyl methyl ether may be added before releasing the base from water solution of naltrexone salt.

If necessary, cyclopentyl methyl ether can be mixed with another suitable solvent, such as alcohols or ketones or a combination thereof. The content of the additional component may be in the range of 0.5% to 95.0%. It is preferred to use alcohols which, thanks to their higher polarity, help to remove more polar impurities, preferably from the group consisting of methanol, ethanol, 2-propanol, n-propanol, 2-butanol, n-butanol, isobutanol, tert-butanol, amyl alcohol, isoamyl alcohol, tert-amyl alcohol, 4-methyl-2-pentanol, or ketones from the group consisting of acetone, butanone, 2-pentanone, 3-pentanone, methyl isobutyl ketone, methyl isopropyl ketone.

Cyclopentyl methyl ether can be used for purification of naltrexone base by trituration, wherein it disposes of impurities in almost the same extent as in the case of crystallization, and pure product is obtained. It is possible to use dry cyclopentyl methyl ether, wet cyclopentyl methyl ether, as well as mixed solvent with major proportion of cyclopentyl methyl ether and with another suitable solvent (the content of cyclopentyl methyl ether from 50.1% to 99.5%) or other solvent with minor content of cyclopentyl methyl ether (however, at least in the amount of 1 molar equivalent for the naltrexone base). The other suitable solvent may be optional solvent or combination from the group consisting of methanol, ethanol, 2-propanol, n-propanol, 2-butanol, n-butanol, isobutanol, tert-butanol, amyl alcohol, tert-amyl alcohol, 4-methyl-2-pentanol or ketones from the group consisting of acetone, butanone, 2-pentanone, 3-pentanone, methyl isobutyl ketone, methyl isopropyl ketone.

A product with high purity and content (more than 98%) is obtained after isolation of naltrexone base from the reaction mixture by extraction with cyclopentyl methyl ether and subsequent crystallization of such solution (also after possible concentration by evaporation).

Additional product of naltrexone base can be obtained by processing of mother liquor after crystallization.

Crystallization in cyclopentyl methyl ether in a mixture with another suitable solvent (for example 10% methanol) also results in a product with high purity and content (more than 98%), and with a yield of more than 80%.

Last but not least, crystallization of naltrexone base from polar solvent (such as methanol, ethanol, 2-propanol, n-propanol, 2-butanol, n-butanol, isobutanol, tert-butanol, amyl alcohol, isoamyl alcohol, tert-amyl alcohol, 4-methyl-2-pentanol or ketones from the group consisting of acetone, butanone, 2-pentanone, 3-pentanone, methyl isobutyl ketone, methyl isopropyl ketone) with addition of cyclopentyl methyl ether (approx. 10% solution of cyclopentyl methyl ether, however, at least 1 molar equivalent of cyclopentyl methyl ether in relation to the naltrexone) provides a product with high yield (>80%) as well as good purity and content.

Extraction of naltrexone base from the reaction mixture may be performed with pure cyclopentyl methyl ether or in combination with another solvent mentioned above, the content of cyclopentyl methyl ether being at least 1 equivalent of the naltrexone base.

The naltrexone base can be precipitated from the solution in cyclopentyl methyl ether in the form of hydrochloride by adding concentrated hydrochloric acid or hydrochloric acid in alcohol (for example, methanol, ethanol, 2-propanol, etc.) or ketone (for example, 2-butanone). Naltrexone is thus obtained in quantitative yield.

Naltrexone base prepared according to the above mentioned procedures can be used for preparation of a parenteral dosage form, such as patch. It can also be used for the preparation of naltrexone salts which are used for the preparation of other dosage forms.

EXAMPLES OF EMBODIMENTS OF THE INVENTION

Table 1 shows the results of purification of a mixture containing 77% of the naltrexone base. These experiments indicate that besides high purification ability, cyclopentyl methyl ether also provides good yields of the product.

TABLE 1

Purification of a mixture of the naltrexone base containing 77% of naltrexone.

| Solvent | Yield (in relation to naltrexone content) | HPLC purity (area %) |
| --- | --- | --- |
| 1. Methyl isobutyl ketone | 13% | — |
| 2. 2-propanol | 69% | 90.34 |
| 3. 2-butanol | 53% | 89.93 |
| 4. Tetrahydrofuran | 0% | — |
| 5. Methyltetrahydrofuran | 19% | — |
| 6. Cyclopentyl methyl ether | 75% | 99.14 |
| 7. Methyl tert-butyl ether | 64% | 94.81 |
| 8. Dibutyl ether | insoluble | — |
| 9. Dibutyl ether/2-propanol 5/1 | 45% | 96.26 |

Example 1

Naltrexone base (10.0 g, weight content >90%) is stirred in cyclopentyl methyl ether (40 mL) for the purpose of trituration. The mixture is cooled below 10° C. following trituration of naltrexone base and the product is filtered by suction, washed with cyclopentyl methyl ether, and dried in a vacuum dryer. 8.05 g of the naltrexone base (87% yield) with HPLC purity >99% and weight content >98% is obtained.

Example 2

By a procedure as in example 1 but using a mixture of cyclopentyl methyl ether (36 mL) and ethanol (4 mL), 7.14 g of naltrexone base (77% yield) with HPLC purity >99% and weight content >98% is obtained.

Example 3

By a procedure as in the example 1 but using a mixture of cyclopentyl methyl ether (30 mL) and acetone (10 mL), 7.88 g of naltrexone base (85% yield) with HPLC purity >99% and weight content >98% is obtained.

Example 4

Naltrexone hydrochloride (10.0 g, weight content >95%) is stirred in a mixture of cyclopentyl methyl ether (80 mL) and ethanol (35 mL) for the purpose of trituration. The mixture is cooled below 10° C. following trituration of naltrexone hydrochloride and the product is filtered by suction, washed with cyclopentyl methyl ether, and dried in a vacuum dryer. 9.25 g of naltrexone hydrochloride (97% yield) with high purity is obtained.

Example 5

Cyclopentyl methyl ether (10-150 mL) is used for dissolution of naltrexone base (10.0 g, weight content 75%) under stirring and gradual heating until naltrexone dissolution. The insoluble portion is filtered off at a higher temperature after dissolution of the naltrexone base and a solution of naltrexone dissolved in cyclopentyl methyl ether is obtained.

Example 6

Cyclopentyl methyl ether (10-150 mL) is used for dissolution of naltrexone base (10.0 g, weight content 90%) under stirring and gradual heating until naltrexone dissolution. The insoluble portion is filtered off at a higher temperature after dissolution of the naltrexone base and a solution of naltrexone dissolved in cyclopentyl methyl ether is obtained.

Example 7

A mixture of cyclopentyl methyl ether (10-150 mL) and methanol (1-15 mL) is used for dissolution of the naltrexone base (10.0 g) under stirring and gradual heating until naltrexone dissolution. After dissolving the naltrexone base, a solution of naltrexone dissolved in a mixture of cyclopentyl methyl ether and methanol is obtained.

Example 8

A mixture of cyclopentyl methyl ether (10-150 mL) and methyl isobutyl ketone (1-15 mL) is used to dissolve the naltrexone base (10.0 g) under stirring and gradual heating until naltrexone dissolution. After dissolution of the naltrexone base, a solution of naltrexone dissolved in the mixture of cyclopentyl methyl ether and methyl isobutyl ketone is obtained.

Example 9

A mixture of cyclopentyl methyl ether (10-40 mL) and methanol (40-60 mL) is used for dissolution of naltrexone hydrochloride (10.0 g) under stirring and gradual heating until naltrexone dissolution. After dissolution of the naltrexone base, a solution of naltrexone hydrochloride dissolved in the mixture of cyclopentyl methyl ether and methanol is obtained.

Example 10

Cyclopentyl methyl ether (60 mL) is added to a suspension of naltrexone base (10.0 g) in water containing inorganic salts and the mixture is heated until two phases form. After the dissolution of the naltrexone base, the aqueous phase is separated and a solution of naltrexone in cyclopentyl methyl ether is obtained by extraction.

Example 11

Cyclopentyl methyl ether (60 mL) is added to an aqueous solution of naltrexone hydrochloride. The aqueous phase is gradually neutralized/alkalized and after neutralization/alkalization, the heterogeneous mixture is heated until two homogenous phases are formed. After dissolution of the naltrexone base, the aqueous phase is separated and a solution of naltrexone in cyclopentyl methyl ether is obtained by extraction.

Example 12

Methanol (10 mL) and cyclopentyl methyl ether (60 mL) are added to a suspension of the naltrexone base (10.0 g) in water containing inorganic salts and the mixture is heated until two phases are formed. After dissolution of the naltrexone base, the aqueous phase is separated and a solution of naltrexone in the mixture of cyclopentyl methyl ether and methanol is obtained by extraction.

Example 13

Ethanol (15 mL) and cyclopentyl methyl ether (50 mL) are added to an aqueous solution of naltrexone hydrochloride. The aqueous phase is gradually neutralized/alkalized and after neutralization/alkalization, the heterogeneous mixture is heated until two homogenous phases are formed. After dissolution of the naltrexone base, the aqueous phase is separated and a solution of naltrexone in the mixture of cyclopentyl methyl ether and ethanol is obtained by extraction.

Example 14

35% aqueous hydrochloric acid is added dropwise to a naltrexone solution (5.0 g) in cyclopentyl methyl ether (50 mL) causing naltrexone hydrochloride to precipitate. The precipitated mixture is dehydrated azeotropically and the precipitate is filtered off with suction. Naltrexone hydrochloride in quantitative yield is obtained.

Example 15

3 M solution of hydrochloric acid in cyclopentyl methyl ether is added dropwise to a naltrexone solution (5.0 g) in cyclopentyl methyl ether (50 mL) causing naltrexone hydrochloride to precipitate. The precipitated mixture is filtered with suction. Naltrexone hydrochloride in quantitative yield is obtained.

Example 16

A solution of hydrochloric acid in isopropanol is added dropwise to a naltrexone solution (5.0 g) in cyclopentyl methyl ether (50 mL) causing naltrexone hydrochloride to precipitate. The precipitated mixture is filtered with suction. Naltrexone hydrochloride in quantitative yield is obtained.

Example 17

A solution of hydrochloric acid in methyl ethyl ketone is added dropwise to a naltrexone solution (5.0 g) in cyclopentyl methyl ether (50 mL) causing naltrexone hydrochloride to precipitate. The precipitated mixture is filtered with suction. Naltrexone hydrochloride in quantitative yield is obtained.

Examples 18

Cyclopentyl methyl ether (40 mL) is used for the dissolution of the naltrexone base (10.0 g, weight content 75%) under stirring and gradual heating until naltrexone dissolution. After dissolution of the naltrexone base, the insoluble portion is filtered off at a higher temperature and the filtrate is stirred under gradual cooling (crystallization occurs). The crystallized product is filtered off with suction, washed with cyclopentyl methyl ether, and dried in a vacuum dryer. 6.25 g of the naltrexone base (81% yield in relation to the content of naltrexone in the substrate) with HPLC purity >97% and weight content >96% is obtained.

Example 19

The naltrexone base (10.0 g, weight content >95%) is stirred in cyclopentyl methyl ether (40 mL) and heated until naltrexone dissolves. After dissolution of the naltrexone base, the warm solution of naltrexone in cyclopentyl methyl ether is stirred while the temperature decreases to room temperature (crystallization occurs). The suspension is cooled below 10° C. and the crystallized product is filtered off with suction, washed with cyclopentyl methyl ether, and dried in a vacuum dryer. 8.05 g of the naltrexone base (85% yield in relation to the content of naltrexone in the substrate) with HPLC purity >99% and weight content >98% is obtained.

Example 20

Cyclopentyl methyl ether (60 mL) is added to a suspension of the naltrexone base (10.0 g) in water containing inorganic salts and the mixture is heated until two phases are formed. After dissolution of the naltrexone base, the warm solution of naltrexone in cyclopentyl methyl ether is separated from the aqueous phase. If necessary, the aqueous phase is extracted with additional cyclopentyl methyl ether. 20 mL of cyclopentyl methyl ether is distilled off (water is separated azeotropically) from the organic layer and the solution of naltrexone in cyclopentyl methyl ether is cooled below 10° C. (crystallization occurs). The crystallized product is filtered off with suction, washed with cyclopentyl methyl ether, and dried in a vacuum dryer. 8.14 g of naltrexone base (representing an 81% yield) with HPLC purity >99% and weight content >98% is obtained.

Example 21

Cyclopentyl methyl ether (60 mL) is added to an aqueous solution of naltrexone hydrochloride. The aqueous phase is gradually neutralized/alkalized and after neutralization/alkalization, the heterogeneous mixture is heated until two homogeneous phases are formed. After dissolution of the naltrexone base, the warm solution of naltrexone in cyclopentyl methyl ether is separated from the aqueous phase. If necessary, the aqueous phase is extracted with additional cyclopentyl methyl ether. The separated organic layer is cooled below 10° C. (crystallization occurs). The crystallized product is filtered off with suction, washed with cyclopentyl methyl ether, and dried in a vacuum dryer. 8.31 g of the naltrexone base (85% yield) with HPLC purity >99% and weight content >98% is obtained.

Example 22

The naltrexone base (10.0 g, weight content >95%) is stirred in a mixture of cyclopentyl methyl ether (21 mL) and methanol (19 mL) and heated until the base dissolves. Following the dissolution of the naltrexone base, the warm solution of naltrexone in the mixture is stirred while the temperature decreases to room temperature (crystallization occurs). The suspension is cooled below 10° C. and the crystallized product is filtered off with suction, washed with cyclopentyl methyl ether, and dried in a vacuum dryer. 7.77 g of the naltrexone base (82% yield) with HPLC purity >99% and weight content >98% is obtained.

Example 23

The naltrexone base (10.0 g, weight content >95%) is stirred in a mixture of cyclopentyl methyl ether (40 mL) and methanol (0.2 mL) and heated until the base dissolves. Following dissolution of the naltrexone base, the warm solution of naltrexone is stirred while the temperature decreases to room temperature (crystallization occurs). The suspension is cooled below 10° C. and the crystallized product is filtered off with suction, washed with cyclopentyl methyl ether, and dried in a vacuum dryer. 7.98 g of the naltrexone base (84% yield) with HPLC purity >99% and weight content >98% is obtained.

Example 24

The naltrexone base (10.0 g, weight content >95%) is stirred in a mixture of cyclopentyl methyl ether (3.3 mL, 1 molar equivalent for the naltrexone base) and methanol (33 mL) and heated until naltrexone dissolves. After dissolution of the naltrexone base, the warm solution of naltrexone in cyclopentyl methyl ether is stirred while the temperature decreases to room temperature (crystallization occurs). The suspension is cooled below 10° C. and the crystallized product is filtered off with suction, washed with cyclopentyl methyl ether, and dried in a vacuum dryer. 7.49 g of naltrexone base (79% yield) with HPLC purity >99% and weight content >98% is obtained.

Example 25

By the same procedure as in the example 23, but using the mixture of cyclopentyl methyl ether (95%) and methanol (5%), 8.01 g of naltrexone base (80% yield) with HPLC purity >99% and weight content >98% is obtained.

Example 26

By the same procedure as in the example 23, but using the mixture of cyclopentyl methyl ether (10%) and amyl alcohol (90%), 7.96 g of naltrexone base (80% yield) with HPLC purity >99% and weight content >98% is obtained.

Example 27

The naltrexone base (10.0 g, weight content >90%) is stirred in dry cyclopentyl methyl ether (40 mL). The suspension is cooled below 10° C. after trituration of naltrexone base and the product is filtered off with suction, washed with cyclopentyl methyl ether, and dried in a vacuum dryer. 8.05 g of naltrexone base (87% yield) with HPLC purity >99% and weight content >98% is obtained.

Example 28

By the procedure as in the example 27, but using wet cyclopentyl methyl ether (water content 0.35%), 8.35 g of the naltrexone base (90% yield) with HPLC purity >99% and weight content >98% is obtained.

Example 29

By the procedure as in the example 27, but using a mixture of cyclopentyl methyl ether and methanol (50.1/49.9), 7.14 g of the naltrexone base (77% yield) with HPLC purity >99% and weight content >98% is obtained.

Example 30

By the procedure as in the example 27, but using a mixture of cyclopentyl methyl ether and methyl ethyl ketone (75/25), 8.44 g of the naltrexone base (91% yield) with HPLC purity >99% and weight content >98% is obtained.

Example 31

By the procedure as in the example 27, but using a mixture of cyclopentyl methyl ether and methanol (99.5/0.5), 7.88 g of naltrexone base (85% yield) with HPLC purity >99% and weight content >98% is obtained.

Example 32

By the procedure as in the example 27, but using a mixture of cyclopentyl methyl ether (1 molar equivalent for the content of the naltrexone base) and methanol, 7.31 g of naltrexone base (79% yield) with HPLC purity >99% and weight content >98% is obtained.

Example 33

The naltrexone base (10.0 g, weight content >95%) is stirred in cyclopentyl methyl ether (40 mL) and heated until naltrexone dissolves. After dissolution of the naltrexone base, the warm solution of naltrexone in cyclopentyl methyl ether is stirred while the temperature decreases to room temperature (crystallization occurs). The suspension is cooled below 10° C. and the crystallized product is filtered off with suction, washed with cyclopentyl methyl ether, and dried in a vacuum dryer. 8.05 g of the naltrexone base (85% yield in relation to naltrexone content in the substrate) with HPLC purity >99% and weight content >98% is obtained. The naltrexone base thus obtained is used for a parenteral dosage form, such as a patch. The naltrexone base thus obtained is used for the preparation of naltrexone salts useful in dosage forms other than patches.

The invention claimed is:
1. A method for the isolation or purification of naltrexone base or naltrexone salts, said method comprising
    mixing said naltrexone base or naltrexone salts with cyclopentyl methyl ether (CPME) to form a mixture thereof, and subjecting the mixture of CPME and naltrexone base or naltrexone salts to at least one of the following steps:
triturating,
suspension,
dissolution,
extraction,
precipitation, and
crystallization;
wherein the CPME is the only solvent or CPME is mixed with at least one additional solvent selected from the group consisting of methanol, ethanol, isopropanol, amyl alcohol, acetone and methyl isobutyl ketone.

2. The method according to claim 1, further comprising triturating the naltrexone base or naltrexone salts in CPME.

3. The method according to claim 1, further comprising suspending the naltrexone base or naltrexone salts in CPME.

4. The method according to claim 1, further comprising dissolving the naltrexone base or naltrexone salts in CPME.

5. The method according to claim 1, further comprising extracting the naltrexone base or naltrexone salts from CPME.

6. The method according to claim 1, further comprising precipitating the naltrexone base or naltrexone salts in CPME.

7. The method according to claim 1, further comprising crystallizing naltrexone base or naltrexone salts in CPME.

8. The method according to claim 1, wherein the method is performed in an anhydrous environment.

9. The method according to claim 1, wherein the method is performed in the presence of water.

10. The method according to claim 1, further comprising triturating the naltrexone base or naltrexone salts in the at least one additional solvent.

11. The method according to claim 1, further comprising suspending the naltrexone base or naltrexone salts in the at least one additional solvent.

12. The method according to claim 1, further comprising dissolving the naltrexone base or naltrexone salts in the at least one additional solvent.

13. The method according to claim 1, further comprising extracting the naltrexone base or naltrexone salts from the at least one additional solvent.

14. The method according to claim 1, further comprising precipitating the naltrexone base or naltrexone salts in the at least one additional solvent.

15. The method according to claim 1, further comprising crystallizing the naltrexone base or naltrexone salts in the at least one additional solvent.

* * * * *